(12) United States Patent
Bauer

(10) Patent No.: US 8,288,088 B2
(45) Date of Patent: Oct. 16, 2012

(54) METHOD FOR INDUCING TUMOR APOPTOSIS BY INCREASING NITRIC OXIDE LEVELS

(75) Inventor: Georg Bauer, Freiburg (DE)

(73) Assignee: Universitatsklinikum Freiburg, Freiburg (DE)

( * ) Notice: Subject to any disclaimer, the term of this patent is extended or adjusted under 35 U.S.C. 154(b) by 782 days.

(21) Appl. No.: 12/438,791

(22) PCT Filed: Aug. 7, 2007

(86) PCT No.: PCT/EP2007/006964
§ 371 (c)(1),
(2), (4) Date: Feb. 25, 2009

(87) PCT Pub. No.: WO2008/071242
PCT Pub. Date: Jun. 19, 2008

(65) Prior Publication Data
US 2009/0264398 A1    Oct. 22, 2009

(30) Foreign Application Priority Data
Aug. 30, 2006    (EP) .................................. 06018120

(51) Int. Cl.
*C12Q 1/00* (2006.01)
*C12N 5/02* (2006.01)
(52) U.S. Cl. ............................................ 435/4; 435/325
(58) Field of Classification Search .................. None
See application file for complete search history.

(56) References Cited

U.S. PATENT DOCUMENTS

| 5,565,478 A | 10/1996 | Kohn et al. | |
|---|---|---|---|
| 5,795,790 A | 8/1998 | Schinstine et al. | |
| 2009/0264398 A1 * | 10/2009 | Bauer | 514/210.01 |

FOREIGN PATENT DOCUMENTS

| DE | 199 63 052 | 6/2001 |
|---|---|---|
| WO | WO 97/05873 | 2/1997 |
| WO | WO 98/04681 | 2/1998 |
| WO | WO 03/073990 | 9/2003 |
| WO | WO 2004/073623 | 9/2004 |
| WO | WO 2005/000208 | 1/2005 |
| WO | WO 2005/117545 | 12/2005 |

OTHER PUBLICATIONS

Buga, G M et al, "NG-Hydroxy-L-Arginine and Nitric Oxide Inhibit CaCo-2 Tumor Cell Proliferation by Distinct Mechanisms", American Journal of Physiology, vol. 44 (4), pp. 1256-1264 (Oct. 1998).
Frantisek, Franek et al, "Antiapoptotic and Proapoptotic Action of Various Amino Acids and Analogs in Starving MOLT-4 Cells", Archives of Biochemistry and Biophysics, vol. 398 (1), pp. 141-146 (Feb. 2002).
Frantisek, Franek et al, "Protection of B Lymphocyte Hybridoma Against Starvation-Induced Apoptosis: Survival-Signal Role of Some Amino Acids", Immunology Letters, vol. 52 (2-3), pp. 139-144 (1996).

* cited by examiner

*Primary Examiner* — Michael Burkhart
(74) *Attorney, Agent, or Firm* — Chalin A. Smith; Smith Patenting Consulting, LLC

(57) ABSTRACT

The present invention refers to a method for inducing tumor apoptosis by influencing the ROS (reactive oxygen species) signaling pathway in tumor cells. Increasing the level of ROS leads to the selective inactivation of a tumor cell catalase and subsequently to an apoptosis of these cells. The level of ROS can be increased by increasing the level of nitric oxide through inhibition of the enzymes nitric oxide dioxygenase or arginase.
According to the present invention inhibitors of the nitric oxide dioxygenase or arginase can be used for the manufacture of a medicament for the treatment of cancer. The present invention further provides a method for identifying compounds which can be used for the treatment of cancer, wherein the method allows to specifically identify compounds which induce apoptosis through the ROS signaling pathway. The present invention also provides a kit for identifying compounds which induce tumor apoptosis by inactivating a catalase on the tumor cell surface.

6 Claims, 12 Drawing Sheets

Figure 5 A-D
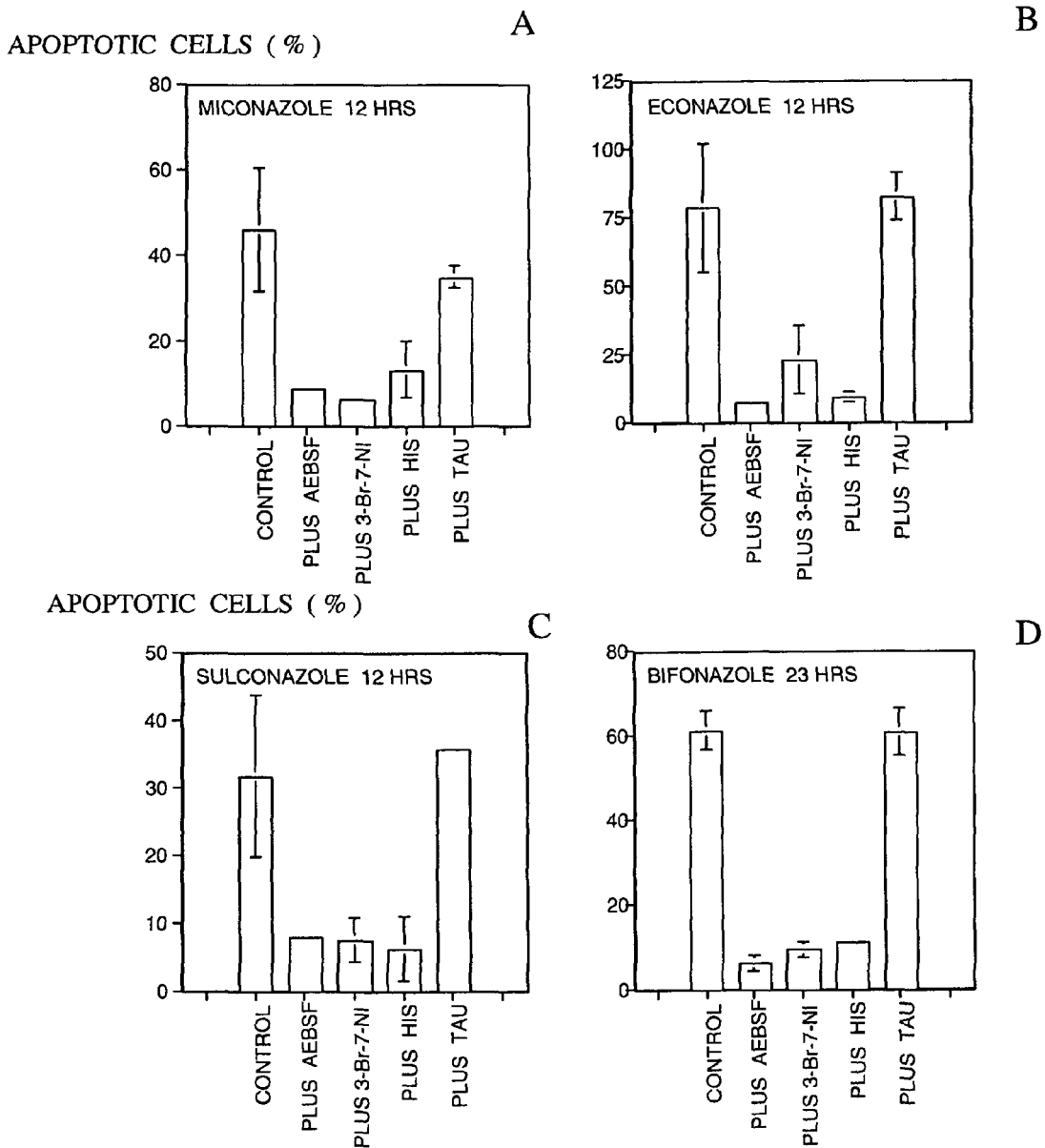

Figure 5 E-H
APOPTOTIC CELLS (%)
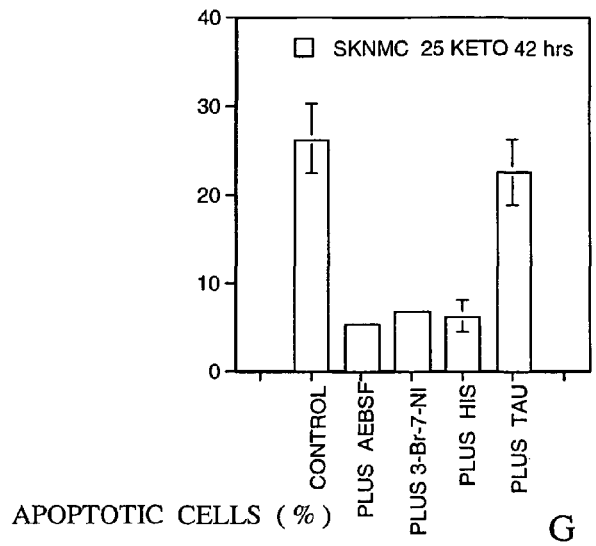
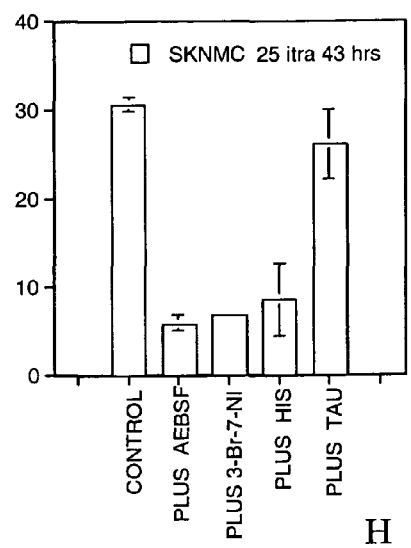
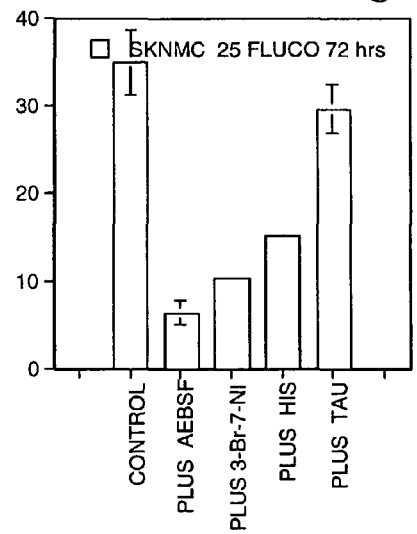
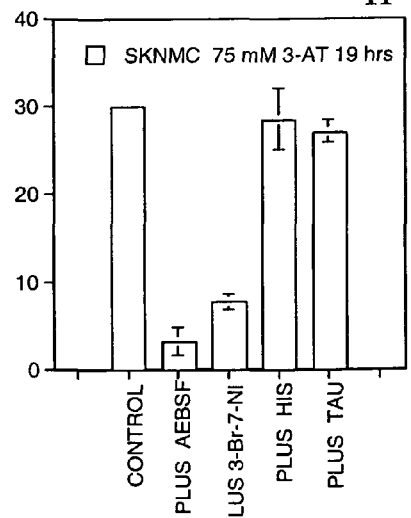

METHOD FOR INDUCING TUMOR APOPTOSIS BY INCREASING NITRIC OXIDE LEVELS

This application corresponds to the national phase of International Application No. PCT/E07/006964, filed Aug. 7, 2007, which, in turn, claims priority to European Patent Application No. 06.18120.3, filed Aug. 30, 2006, the contents of both of which are incorporated by reference herein in their entirety.

The present invention refers to a method for inducing tumor apoptosis by influencing the ROS (reactive oxygen species) signaling pathway in tumor cells. Increasing the level of ROS leads to the selective inactivation of a tumor cell catalase and subsequently to an apoptosis of these cells. The level of ROS can be increased by increasing the level of nitric oxide through inhibition of the enzymes nitric oxide dioxygenase or arginase. According to the present invention inhibitors of the nitric oxide dioxygenase or arginase can be used for the manufacture of a medicament for the treatment of cancer. The present invention further provides a method for identifying compounds which can be used for the treatment of cancer, wherein the method allows to specifically identify compounds which induce apoptosis through the ROS signaling pathway. The present invention also provides a kit for identifying compounds which induce tumor apoptosis by inactivating a catalase on the tumor cell surface.

WO 2005/117545 discloses that NO catabolic pathways may provide immune resistance to carcinomas, and thus serve as novel targets for cancer intervention. According to this document, the NO catabolic pathways can be influenced by using nitric oxide dioxygenase inhibitors in an amount sufficient to increase the intra-cellular concentration of nitric oxide (NO). However, WO 2005/117545 does not disclose the selective tumor cell apoptosis by destroying the tumor cell catalase and mediating the ROS signaling pathway. The present invention is not based on an immunological effect of nitric oxide dioxygenase inhibitors but on the selective destruction of tumor cells.

WO 2005/000208 refers to the use of a combination of an HMG—CoA reductase inhibitor and an azole for the treatment of a neoplasm. The use of a combination of those two compounds was based on the finding that azoles enhance the anti-proliferative activity of HMG—CoA reductase inhibitors against cancer cells in vitro.

Furthermore, WO 2004/073623 refers to a method of treating a subject having elevated arginase as a symptom or cause of a disorder. Such a treatment comprises administering an arginase inhibitor in order to enhance the arginine bioavailability in the subject. However, there is no teaching in this document that arginase inhibitors can be used to destroy tumor cell catalase and induce an tumor cell selective cell apoptosis.

WO 03/03990 refers to the use of a compound that decreases the production of a protein involved in arginine metabolism in the preparation of a medicament for treating asthma or allergies. Any effect of arginase inhibitors on the tumor cell catalase or the ROS signaling pathway is not described in this document.

Buga et al. (*Am. J. Physiol.*, 1989, pages 1256-1264) describe the use of $N^G$-hydroxy-L-arginine (NOHA) for inhibiting Caco-2 tumor cell proliferation. The effect of arginase inhibitors on selective tumor cell apoptosis as used in the present invention is not indicated in this document.

WO 97/05873 also discloses the use of fluconazole (a nitric oxide dioxygenase inhibitor) for the inhibition of the growth of tumor cells due to the properties of fluconazole to potentiate the effect of a chemotherapeutic agent. Similarly, U.S. Pat. No. 5,565,478 refers to the augmentation of the activity of paclitaxel by ketoconazole when used for the treatment of cancer.

Furthermore, DE 199 63 052 discloses the use of azoles for the prevention of skin cancer, mediated by UV-radiation. None of the above documents discloses a selective tumor cell apoptosis. Especially, there is no teaching to use a combination of an nitric oxide dioxygenase inhibitor and an arginase inhibitor for the treatment of cancer.

It is furthermore known from the experimental work of Irani et al. (Science 1997; 275:1649-1652) that oncogenic transformation of cells causes constitutive generation of extracellular superoxide anions through a membrane associated NADPH oxidase. In the following, tumor cells are distinguished from transformed cells. Transformed cells can be defined as cells which have been transformed in vitro, either by expression of specific oncogenes, by chemical or physical carcinogenic changes or spontaneous transformation, and possess potential for tumor formation. Tumor cells as well as transformed cells produce extracellular superoxide anions. The superoxide anions react to hydrogen peroxide in a close distance to the cell surface. Hydrogen peroxide is long-lived and far-ranging, but nevertheless much more reactive than superoxide anions. For example, superoxide anions do not induce apoptosis directly, but hydrogen peroxide does, if a certain concentration is reached.

Furthermore it is known from Engelmann and Bauer (Anticancer Research 2000; 20:2297-2306) that not transformed fibroblasts, which have been stimulated with TGF (transforming growth factor)-beta or FGF (fibroblast growth factor), can serve as a intercellular effector cell and induce apoptosis to transformed cell. Not transformed fibroblasts are not damaged.

It is known from Bauer et al. (Prostaglandines, Leukotrienes and Essential Fatty Acids 2002; 66:41-56) that the transformed cells release superoxide anions, which exhibit signaling functions such as regulation of proliferation and maintenance of the transformed state. The dismutation product hydrogen peroxide regulates the intracellular level of catalase, whose activity has been observed to be upregulated in certain transformed cells. After glutathione depletion, the transformed cell-derived reactive oxygen species (ROS) exhibit apoptosis-inducing potential through the metal-catalyzed Haber-Weiss reaction, which turns hydrogen peroxide into the highly reactive, extremely short-lived and short-ranging hydroxyl radical from.

Moreover, transformed cell-derived ROS represent key elements for selective and efficient apoptosis induction by natural antitumor systems (such as fibroblasts, granulocytes and macrophages). These effector cells release peroxidase, which utilizes target cell-derived hydrogen peroxide for HOCl synthesis. In a second step, HOCl interacts with target cell-derived superoxide anions and forms apoptosis-inducing hydroxyl radicals (HOCl pathway).

In a parallel signaling pathway, effector cell-derived NO interacts with target cell-derived superoxide anions and generates the apoptosis inducer peroxynitrite. Therefore, transformed cell-derived ROS determine transformed cells as selective targets for induction of apoptosis by these effector systems. It was therefore proposed that transformed cell-derived ROS interact with associated cells to exhibit directed and specific signaling functions, some of which are beneficial and some of which can become detrimental to transformed cells.

WO 2005/056048 discloses that superoxide anions react with nitric oxide and produce the highly reactive peroxynitrite in close distance to the transformed cells. Furthermore tumor cells comprise a catalase on the cell surface which deactivates peroxynitrite and therefore inhibits apoptosis. It was found that the inhibition of this catalase consequently prevents the decomposition of peroxynitrite and leads to apoptosis in tumor cells.

WO 2005/056048 furthermore discloses that the generation of hydrogen peroxide from superoxide anions on the surface is not sufficient to induce apoptosis in these cells. As described above, the hydrogen peroxide is transformed into hypochlorous acid by a peroxidase and the subsequent interaction of hypochlorous acid with superoxide anions results in the formation of hydroxyl radicals. It was found that the inhibition of a catalase of the tumor cells which also reacts with hydrogen peroxide leads to a higher concentration of hydrogen peroxide and hydroxyl radicals respectively. The increased levels of apoptosis inducers subsequently lead to a selective apoptosis in the tumor cells. WO 2005/056048 therefore provides a method for specifically increasing the sensitivity of tumor cells against apoptosis by inhibiting the catalase of the tumor cells.

Contrary to the inhibition of the catalase, the present invention is based on experimental results, which have shown that the tumor cell catalase can also be inactivated in order to induce selective apoptosis to tumor cells. Although the catalase of the tumor cells is able to inactivate peroxynitrite, it was found in the present experimental studies that this catalase itself can be inactivated if the peroxynitrite level is significantly increased. This will be explained in the following.

Peroxynitrite is formed by the reaction of nitric oxide with superoxide anions. Arginine is a substrate for the arginase and for the NO synthase, whereas the inhibition of the arginase provides more substrate for the NO synthase and therefore increases the NO production.

The NO dioxygenase has NO as a substrate, whereas the inhibition of the NO dioxygenase increases the NO level by preventing this enzyme to inactivate nitric oxide. Increasing the NO (nitric oxide) level in close distance to the cell surface by inhibiting the enzyme arginase or the enzyme NO dioxygenase leads to a higher concentration of peroxynitrite (NO/peroxynitrite pathway).

The experiments which have been performed during the present invention prove that peroxynitrite can react with hydrogen peroxide to form a reactive oxygen species. This reactive oxygen species is singlet oxygen which reacts with histidine. Histidine plays an important role in the active center of the tumor specific catalase, whereby the reaction of singlet oxygen with histidine inactivates the catalase, which is then not able to inactivate peroxynitrite or hydrogen peroxide anymore. The present invention therefore provides a method for a selective inactivation of the catalase on the surface of tumor cells.

Accordingly, the high level of peroxynitrite leads to apoptosis of the tumor cell. The mechanism of increasing the nitric oxide level by inhibition of enzymes, the formation of peroxynitrite, the formation of hydrogen peroxide and the formation of hydroxyl radicals from hydrogen peroxide is disclosed in FIG. 1 in more detail. Furthermore example 1 comprises experimental proof that the reactive oxygen species singlet oxygen is able to inactivate the catalase of the tumor cells. The experiments show that the addition of histidine prevents apoptosis in tumor cells by scavenging of singlet oxygen. The histidine, like the histidine from the catalase, reacts with singlet oxygen and thus prevents catalase inactivation and subsequent intercellular ROS signaling. The inhibition of apoptosis by histidine addition therefore allows to determine whether or not the apoptosis is based on singlet oxygen-dependent catalase inactivation followed by intercellular ROS signaling.

Furthermore it has surprisingly been found that apoptosis based on the ROS signaling can be directly induced in tumor cells without any signaling from the nontransformed effector cells being necessary. Therefore it was possible to develop a method for testing the apoptosis inducing properties of compounds by using tumor cells without the requirement of not transformed effector cells being present.

The method according to the present invention is based on the finding that the ROS-mediated apoptosis can be inhibited by histidine addition due to preserving the catalase from inactivation. It is furthermore possible to inhibit the ROS signaling pathway by decreasing the level of e.g. superoxide anions, hydrogen peroxide, hypochlorous acid, hydroxyl radicals, nitric oxide or peroxynitrite, which also take part in the ROS based signaling mechanism or through inhibition of peroxidase. The new method can therefore be used for identifying compounds which induce apoptosis by the ROS signaling pathway. This is described in more detail in the following.

The method for identifying suitable compounds comprises a first step of determining whether or not a compound induces apoptosis in tumor cells. A second step is necessary to determine whether the induction of apoptosis is based on the formation of singlet oxygen, followed by catalase inactivation and intercellular ROS signaling. This is achieved by addition of histidine, which is able to scavenge singlet oxygen (Tyrrell et al, Methods 1997; 11: 313-138). If histidine lowers the apoptosis induction in tumor cells, proof is given that the compound induces apoptosis via formation of singlet oxygen. Additionally it is determined whether the compounds which induce apoptosis based on the ROS signaling pathway are toxic to normal diploid fibroblasts.

The compounds which induce apoptosis in tumor cells, based on ROS species formation, can then be analyzed in a third step. This third step is optional and can be performed in order to determine whether the apoptosis induction, which can be inhibited by histidine addition, is based on the tumor cell specific ROS signaling pathway. This is the case, if the inactivation of other species which participate in the ROS signaling pathway prevents apoptosis in tumor cells.

The present invention therefore provides a new approach for treating cancer by increasing the level of reactive oxygen species by increasing the NO level and thereby specifically inactivating the catalase of the tumor cells, which normally inactivates the apoptosis inducer peroxynitrite. The peroxynitrite or hypochlorous acid/hydroxyl radicals derived from hydrogen peroxide then specifically damage the tumor cells.

Further experimental data surprisingly indicated that the well known compound taxol exerts anti-cancer activity through the ROS signaling pathway. A combination of taxol with arginase inhibitors or NO dioxygenase inhibitors therefore provides a much more effective anti-cancer treatment due to a more efficient inhibition of the ROS signaling by inactivating different species which participate in the ROS signaling pathway.

The present invention therefore relates to the use of a nitric oxide dioxygenase inhibitor for the manufacture of a medicament for the treatment of cancer, wherein the nitric oxide dioxygenase inhibitor reduces the enzyme activity for catalyzing the formation of nitrate from nitric oxide.

In a preferred embodiment of the invention, the nitric oxide dioxygenase inhibitor is selected from the group consisting of itraconazole, fluconazole, econazole, bifonazole, ketoconazole, sulconazole, miconazole, hydraconazole, exonazole and zylconazole, further preferred of itraconazole, fluconazole, econazole, bifonazole, ketoconazole, sulconazole and miconazole.

It is even more preferred to use itraconazole or miconazole as the nitric oxide dioxygenase inhibitor.

In another embodiment of the invention the medicament further comprises an arginase inhibitor, wherein the arginase inhibitor reduces the enzyme activity for catalyzing the formation of citrulline from arginine.

It is preferred that the arginase inhibitor is selected from the group consisting of (S)-(2-boronoethyl)-L-cysteine (BEC), 2(S)-amino-6-boronohexanoic acid (ABHA), NOHA/L-HO-Arg ($N^G$-hydroxy-L-arginine), nor-NOHA/L-2-amino-(4-(2'hydroxyguanidino)butyric acid ($N^{omega}$-hydroxy-nor-L-arginine), and DL-alfa-difluoromethylornithine (DFMO). The most preferred arginase inhibitor is norNOHA.

In addition it is preferred that the molar ratio of nitric oxide dioxygenase/arginase inhibitor is between 10:1 and 1:10, preferably in the range from 10:1-4:1; 4:1-1:1; 1:1-1:4 and 1:4-1:10.

In a further embodiment, the medicament additionally comprises Taxol.

The present invention also provides a method for identifying compounds which induce tumor apoptosis by inactivating a catalase on the tumor cell surface comprising a first step of:
contacting the compounds with tumor cells or transformed cells, preferably tumor cells, and selecting compounds which induce apoptosis, and
a second step of:
contacting apoptosis inducing compounds identified in the first step with tumor cells or transformed cells, preferably tumor cells, in a medium preferably comprising 1-10 mM, further preferred 1-5 mM, even more preferred 2-4 mM, and most preferred 2 mM L-histidine (from a stock solution of 20 mM in tissue culture medium) and selecting compounds which do not induce apoptosis in the cells under this condition.

It is preferred that the first step comprises supplying TGF-β to the cells.

It is further preferred to perform the method without non-tumor or not transformed cells being present.

In another embodiment, the method comprises the step of determining whether the compounds are toxic for non-tumor cells.

It is preferred that the method further comprises the step of determining whether the inhibition of tumor apoptosis by histidine is based on the ROS (reactive oxygen species) signaling.

In another embodiment, the step of analyzing the effect on the ROS signaling is performed by contacting the compounds with tumor cells and supplying a compound, which is able to lower the level of one compound selected from the group consisting of: superoxide anions, hydrogen peroxide, HOCl, hydroxyl radical, nitric oxide and peroxynitrite. This is achieved by addition of specific scavengers or inactivators or through genetic knock down of key enzymes like NADPH oxidase, NO synthase or peroxidase using small interfering RNA (siRNA). Superoxide anions are scavenged by superoxide dismutase (100 U/ml). Superoxide anion generation by NADPH oxidase is inhibited by 4-(2-aminoethyl)benzenesulfonyl fluoride (AEBSF, 100 µM). Hydrogen peroxide is destroyed by catalase (100 U/ml). Hypochlorous acid is scavenged by taurine (50 mM). Hydroxyl radicals are scavenged by 400 µM sodium terephthalate or 10 mM mannitol. Peroxynitrite is scavenged by 40 µM FeTPPS (5,10,15,20-TETRAKIS (4-sulfonatophenyl)prophyrinato iron(III), chloride). NO synthesis is blocked through addition of 2.4 mM L-NAME. The peroxidase reaction, leading to the formation of hypochlorous acid is inhibited by 150 µM aminobenzoyyl hydrazide, a mechanism-based peroxidase inhibitor. Transfection of siRNA for iNOS (NOS=nitric oxide synthase) or nNOS (in the case of neuronal tumor cells) inhibits the expression of NO synthetase and thus abrogates NO synthesis. Transfection with siRNA against duox prevents expression of the crucial peroxidase and thus prevents HOCl synthesis. Transfection with siRNA against Nox-1 (NADPH oxidase 1) prevents expression of NADPH oxidase and thus prevents superoxide anion generation. Whether compounds are suitable for analyzing the effect on the ROS signaling depends on the specific tumor cells used in the test. Tumor cells may utilize the HOCl signaling pathway alone, the NO signaling pathway alone or both signaling pathways. A compound which lowers the level of the above-indicated compounds is suitable for the step of analyzing the effect on the ROS signaling, if the compound blocks at least one of the pathways utilized by the tumor cell. If the tumor apoptosis-inducing properties are inhibited by the compound, proof is given that the test compounds induce tumor apoptosis by mediating the ROS signaling pathway. The compounds which induce tumor apoptosis by mediating the ROS signaling pathway might be effective as anti-tumor medicaments.

In a preferred embodiment, the step of analyzing the effect on the ROS signaling is performed by contacting the compounds with tumor cells and supplying one compound from the group of compounds that inhibit superoxide anion synthesis or scavenge superoxide anions (i.e. AEBSF (100 µM) or SOD (100 U/ml)) in combination with at least one compound from the group of compounds that interfere with the HOCl signaling pathway (i.e. the inhibitor of peroxidase (ABH, 150 µM; catalase (100 U/ml), the HOCl scavenger taurine (50 mM) and the hydroxyl radical scavenger mannitol (10 mM) or one compound from the group of compounds that interfere with the NO signaling pathway (i.e. the inhibitor of NO synthase L-NAME (2.4 mM) or other known synthase inhibitors and the peroxynitrite decomposition catalyst FeTPPS (40 µM)). Specific intracellular ROS signaling is confirmed when apoptosis induction by the test compound is inhibited by application of one inhibitor of the compounds that interfere with superoxide anions in combination with at least one of the compounds that interfere either with the HOCl signaling pathway or the NO signaling pathway. The suitable combination of compounds for a certain tumor cell in the test has to be determined before starting the test. Tumor cells may utilize 1) both signaling pathways, 2) the HOCl signaling pathway alone, or 3) the NO signaling pathway alone, dependent on their enzyme setup. The test has to be performed with a superoxide anion synthesis inhibitor or superoxide anion scavenger in combination with at least one HOCl signaling pathway inhibitor (indicated above), if the cells utilize the HOCl signaling pathway. If the tumor cell utilizes the NO signaling pathway, an NO signaling pathway inhibitor (indicated above) is used instead of the HOCl signaling pathway inhibitor. If the tumor cell utilizes both signaling pathways, HOCl or NO signaling pathway inhibitors can be used, preferably at least one inhibitor of each of the two signaling pathways is used.

It is even further preferred to use at least one inhibitor of each of the two signaling pathways, if the tumor cell utilizes both pathways or if the test is performed without knowing which signaling pathway(s) is/are utilized by the tumor cells.

If the above-indicated combinations of compounds inhibit or reduce the apoptosis-inducing properties of the test compounds, proof is given that the apoptosis induction is mediated by ROS signaling.

The present invention further relates to a kit for identifying compounds according to the method as described above, which induces tumor cell apoptosis by inactivating a catalase on the tumor cell surface, comprising tumor cells, TGF-beta, histidine and a compound which is able to lower the level of one compound selected from the group consisting of: superoxide anion, hydrogen peroxide, hypochlorous acid, hydroxyl radical, nitric oxide, peroxynitrite.

The method according to the present invention is based on increasing the level of reactive oxygen species. This leads to the inactivation of the catalase on the surface of the tumor cells, which subsequently increases the concentration of peroxynitrite and leads to tumor cell apoptosis. The production of reactive oxygen species can be achieved by increasing the level of nitric oxide in the tumor cells by inhibiting the enzyme arginase or NO dioxygenase.

The expression "arginase inhibitor" refers to compounds which lower the effectivity of the enzyme arginase to catalyze the formation of citrulline from arginine and thereby increase the amount of arginine available for the nitric oxide synthase. Experiments to identify compounds suitable for arginase inhibition are well known in the art. Arginase activity can for example be determined by commercially available test systems that determine the activity of arginase through measurement of urea generation from arginine. This standard test can be modified for the detection or arginase inhibitors when a defined concentration of arginase is applied and the decrease of urea generation is determined.

The expression "nitric oxide deoxygenase inhibitor" refers to compounds which lower the effectivity of the enzyme nitric oxide deoxygenase to catalyze the formation of nitrate from nitric oxide and thereby increase the nitric oxide level. Experiments to identify compounds suitable for nitric oxide dioxygenase inhibition are well known in the art. Nitric oxide dioxygenase activity is measured through consumption of nitric oxide, dependent on the presence of molecular oxygen and NADPH (Hallstrom et al., Free Radical Biology & Medicine, 37: 216-228, 2004). Nitric oxide dioxygenase inhibitors are defined as compounds that reduce the consumption of nitric oxide under the conditions of the test system described above.

Any known arginase inhibitors can be used according to the present invention in order to inactivate the catalase and the tumor cell subsequently. Examples for suitable arginase inhibitors are but are not limited to:
(S)-(2-boronoethyl)-L-cysteine (BEC), 2(S)-amino-6-boronohexanoic acid (ABHA, NOHA/L-HO-Arg ($N^G$-hydroxy-L-arginine), nor-NOHA/L-2-amino-(4-(2'hydroxyguanidino)butyric acid ($N^{omega}$-hydroxy-nor-L-arginine), DL-alfa-difluoromethylornithine (DFMO), The preferred arginase inhibitor is norNOHA.

Examples for the nitric oxide dioxygenase inhibitors are: itraconazole, ketoconazole, miconazole, fluconazole, bifonazole, econazole and sulconazole. Preferred nitric oxide dioxygenase inhibitors are itraconazole and miconazole.

It is understood that the present invention is not limited to these examples and can be carried out using any known arginase or NO-dioxygenase inhibitors.

The apoptosis induction and destruction of tumor cells can furthermore be achieved by a combination of one arginase inhibitor selected from the group consisting of: (S)-(2-boronoethyl)-L-cysteine (BEC), 2(S)-amino-6-boronohexanoic acid (ABHA), NOHA/L-HO-Arg ($N^G$-hydroxy-L-arginine), nor-NOHA/L-2-amino-(4-(2'hydroxyguanidino)butyric acid ($N^{omega}$-hydroxy-nor-L-arginine), and DL-alfa-difluoromethylornithine (DFMO) in combination with one nitric oxide dioxygenase inhibitor selected from the group consisting of: itraconazole, fluconazole, econazole, bifonazole, ketoconazole, sulconazole, and miconazole.

In a preferred embodiment, the combination of inhibitors comprises the arginase inhibitor norNOHA and one NO-dioxygenase inhibitor selected from the group consisting of itraconazole, fluconazole, econazole, bifonazole, ketoconazole, sulconazole, and miconazole.

It is especially preferred that the combination of inhibitors is a combination of itraconazole or miconazole with an arginase inhibitor selected from the group consisting of: (S)-(2-boronoethyl)-L-cysteine (BEC), 2(S)-amino-6-boronohexanoic acid (ABHA), NOHA/L-HO-Arg ($N^G$-hydroxy-L-arginine), nor-NOHA/L-2-amino-(4-(2'hydroxyguanidino)butyric acid ($N^{omega}$-hydroxy-nor-L-arginine), and DL-alfa-difluoromethylornithine (DFMO). In addition it is preferred that the molar ratio of nitric oxide dioxygenase/arginase inhibitor is between 10:1 and 1:10, further preferred between 10:1-4:1 further preferred 4:1-1:1, even further preferred 1:1-1:4 and most preferred 1:4-1:10.

In a special embodiment of the invention, a combination of taxol as an anticancer active substance with one NO-dioxygenase inhibitor or one arginase inhibitor is used to selectively induce apoptosis in tumor cells. It is preferred to use a combination of taxole with one NO-dioxygenase inhibitor selected from the group consisting of: itraconazole, fluconazole, econazole, bifonazole, ketoconazole, sulconazole, miconazole for the treatment of cancer. Most preferably, a combination of taxol with itraconazole is used to specifically induce apoptosis in tumor cells.

In another embodiment of the present invention, a combination of taxole and an arginase inhibitor and/or an NO dioxygenase inhibitor is used for the treatment of cancer. In this embodiment, the arginase inhibitor and the NO dioxygenase inhibitor can be any inhibitor as specified above. It is preferred that taxole it used in combination with an NO dioxygenase inhibitor.

In a further aspect of the present invention, a method for identifying compounds which induce apoptosis to tumor cells based on the ROS signaling pathway is provided. The method for identifying compounds comprises two essential steps whereas an additional third step can also be included.

Tumor cells which can be used for the test according to the present invention can be e.g. murine cells, especially L929-cells, human tumor cells like SISO or SHEP, but are not limited to these examples. It has to be pointed out that each tumor cell has a specific preference for ROS-mediated intercellular signaling pathways after inhibition or inactivation of its catalase. For example, in L929 and SISO cells the HOCl pathway is dominating, whereas in neuroblastoma cells like SHEP the NO/peroxynitrite pathway is dominating. Others show both pathways with similar activity. In cell lines with dominating HOCl signaling pathway a shift to dominance of the NO pathway may occur at relatively low concentrations of apoptosis-inducing compounds.

The preference of a given tumor cell line for specific intercellular ROS-mediated signaling pathways is defined by the concentration of peroxidase released by the cells and on their rate of superoxide anion generation, which defines the rate of spontaneous hydrogen peroxide formation through dismutation. If the peroxidase release is low (like in the case of neuroblastoma cell lines, mammary carcinoma cells, ovarial carcinoma cells and others) the HOCl pathway will not be effective and the NO pathway will dominate. Therefore, inhibitors of superoxide anion synthesis, superoxide anion scavengers, inhibitors of NO synthase and scavengers of peroxynitrite will inhibit apoptosis induction, but inhibitors of peroxidase, scavengers of HOCl or hydroxyl radicals will have no or only a marginal effect. If the peroxidase release is high, inhibitors of superoxide anion generation or superoxide anion scavengers, inhibitors of peroxidase, scavengers of HOCl or hydroxyl radicals are able to block apoptosis. If the NO signaling pathway plays a detectable role in parallel to the HOCl pathway it will depend on the complete utilization of hydrogen peroxide by peroxidase. In this case, NO will react with superoxide anions in parallel to the HOCl pathway and contribute to apoptosis induction. This is reflected by the inhibition through inhibitors of NO synthase or peroxynitrite scavengers. If there is a relative excess of hydrogen peroxide in the system, the consumption of NO through hydrogen peroxide will downmodulate the NO signaling pathway.

The preference for certain pathways has to be evaluated before a tumor cell line is used for activity or specificity controls in this context. The preference can be determined through inhibition of the catalase with 3-aminotriazole and the use of scavengers directed against the essential signaling components as outlined in FIG. 1. This determination will show, whether specific inhibitors of the HOCl pathway (peroxidase inhibitors, HOCl scavengers, hydroxyl radical scavengers) and/or inhibitors of the NO signaling pathway (inhibitors of NO synthase, peroxynitrite scavengers) block apoptosis. Inhibition by inhibitors of NADPH oxidase and superoxide anion scavengers is mandatory, as superoxide anions play a central role in both signaling pathways. Therefore, inhibition of apoptosis by inhibitors of NADPH oxidase or superoxide anion scavengers in combination with at least one of the inhibitors from the group of inhibitors of the HOCl or the NO signaling pathway allows to conclude that ROS-mediated intercellular signaling is effective.

Any initial density of the tumor cells is suitable for the method according to the invention, however the kinetics of apoptosis induction is determined by the initial density. An initial density of 25 000 cells per 48 well plate allows the least time-consuming test.

It is preferred that the tumor cells are present in a initial density of 25,000 cells in a 48-well plate (e.g. Costar) in a 200 μl media formulation. The reaction mixtures comprise TGF-beta, which enhances the release of peroxidase. The peroxidase is necessary for intracellular signaling in these cells. Preferably the reaction mixtures comprise at least 20 ng/ml TGF-beta.

The first step comprises contacting tumor cells in media comprising TGF-beta with the test compounds to be analyzed for their properties of apoptosis induction. After a specific incubation time, the extent of apoptosis induction is determined, e.g. after two days. Methods for determining the apoptosis in cells in a quantitative manner are well known in the art and are for example described by Jurgensmeier et al. (Cancer Research 1994; 54:393-398). It is based on the determination of the percentage of cells that show membrane blebbing and nuclear condensation and fragmentation, the hallmarks of apoptosis. These features of apoptotic cells can be determined through phase contrast microscopy or after chromatin staining with fluorescent dyes, followed by fluorescence microscopy. Apoptosis-inducing compounds will lead to a significant increase of cells with the morphological signs of apoptosis compared to untreated control cultures.

For comparison, control samples without the test compound are subjected to the same conditions as described above. After the first step, compounds are selected which display a significantly higher apoptosis induction than the control samples. The testing of the control samples can be carried out with media control or solvent control.

The second step comprises contacting the compounds from step 1 with tumor cells and media comprising TGF-beta according to the conditions described at step 1. Furthermore, histidine is added to these reaction mixtures in order to determine whether the apoptosis induction is based on the action of singlet oxygen. It is preferred that the amount of histidine in the reaction mixture is not more than 2 mM. For comparison, step 2 comprises to perform the same reactions with control samples without histidine. The extent of apoptosis induction is again determined after a specific incubation time, e.g. two days. In step 2, compounds are selected which do not induce tumor apoptosis if histidine is added.

The method for identifying suitable compounds can additionally comprise a third step. The third step comprises contacting the identified compounds from step 2 with normal diploid fibroblasts in order to determine whether these compounds induce apoptosis or other toxic reactions and are therefore not suitable for a medical use. The compounds which do not exert negative effects on normal diploid fibroblasts can be subjected to further experiments.

An additional experiment can comprise to determine whether the inhibitory effect of histidine on the induced apoptosis in step 2 is based on one or two of the two major tumor cell-specific ROS signaling pathways, i.e. the HOCl or the NO/peroxynitrite signaling pathway (FIG. 1). This experiment can be performed by contacting the compounds with tumor cells according to the conditions in step 1 and furthermore providing a compound which is able to lower the level of one compound selected from the group consisting of: superoxide anion, hydrogen peroxide, hypochlorous acid, hydroxyl radical, nitric oxide, peroxynitrite. This is achieved by addition of specific scavengers or inactivators. Superoxide anions are scavenged by superoxide dismutase (100 U/ml) or their generation by NADPH oxidase is inhibited by 50 μg/ml apocynine or 100 μM AEBSF (4-(2-aminoethyl)-benzenesulfonylfluoride). Hydrogen peroxide is destroyed by catalase (100 U/ml). Hypochlorous acid is scavenged by taurine (50 mM). Hydroxyl radicals are scavenged by 400 μM sodium terephthalate or 1 mM mannitol. Peroxynitrite is scavenged by 40 μM FeTPPS. NO synthesis is blocked through addition or 2.4 mM L-NAME ($N^G$-nitro-L-arginine-methylester). The peroxidase reaction, leading to the formation of hypochlorous acid is inhibited by 150 μM aminobenzoyl hydrazide, a mechanism-based peroxidase inhibitor. If the apoptosis induction can be inhibited by lowering one of the compounds which participates in the ROS signaling pathway, proof is given that the apoptosis induction is based on the ROS signaling pathway.

The dashed lines indicate the percentage of apoptotic cells obtained when the tumor cell catalase was blocked by 25 mM 23-Aminotriazole (3-AT). In contrast to itraconazole-mediated apoptosis induction, induction by direct catalase inhibition through 3-AT was not blocked by histidine.

Figure 4:
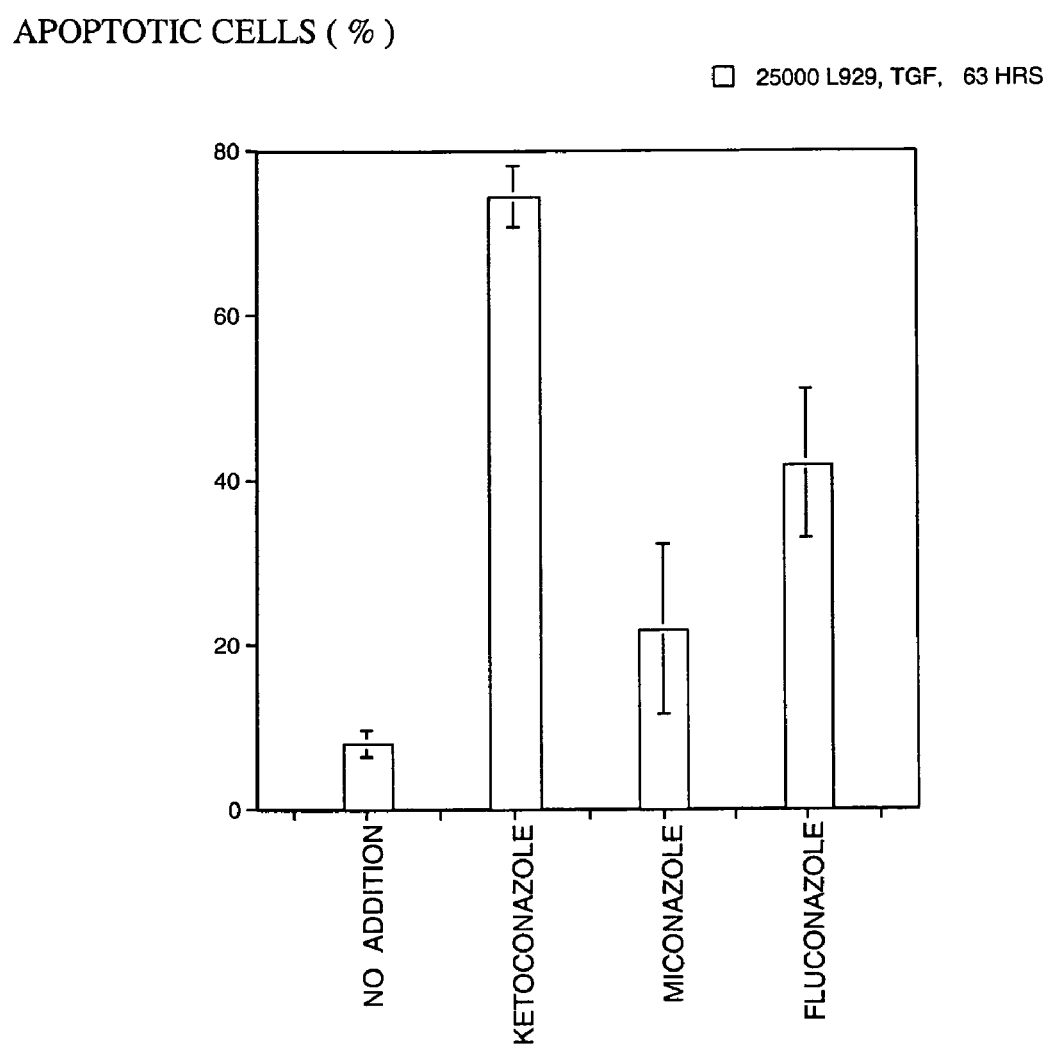

FIG. 4 discloses experimental data obtained with 25000 L929 cells in 48 well tissue culture clusters in the presence of 20 ng/ml TGF-beta. "No addition" represents the control without addition of compound. Ketoconazole, miconazole and fluconazole were added at a final concentration of 12.5 µg/ml. The percentage of apoptotic cells was determined after 63 hrs. The experiment demonstrates the apoptosis inducing potential of the azoles.

FIG. 5 discloses experimental data obtained with 25 000 SKNMC cells (human neuroblastoma) in 48 well tissue culture clusters (without addition of TGF-beta). Control assays did not receive apoptosis-inducing compounds and showed a constant background of apoptosis of less than 1 percent (data not shown). Assays received 12.5 µg/ml of miconazole (A), econazole (B), sulconazole (C), bifonazole (D), or 25 µg/ml of ketoconazole (E), itraconazole (F), fluconazole (G) or 75 mM of the catalase inhibitor 3-AT. Control assays contained the respective compound in the absence of any inhibitors. Parallel assays contained either 200 µM of the NADPH (nicotinamide adenine dinucleotide phosphate) oxidase inhibitor AEBSF, 10 µM of the nNOS-specific NO synthetase inhibitor 3-Br-7-Ni (3-bromo-7-nitroindazole), 2 mM of the singlet oxygen scavenger histidine or 50 mM of the HOCl scavenger taurine. The percentage of apoptotic cells was determined at the indicated time points. The experiment demonstrates that all azoles and the catalase inhibitor 3-AT induced apoptosis in the tumor cells to a significant extent. For all inducers, apoptosis induction was dependent on superoxide anion generation and NO synthesis, as it was blocked by AEBSF and 3-Br-7-Ni respectively. In contrast to the NO/peroxynitrite pathway, the HOCl pathway played no role for apoptosis induction in this particular line. Apoptosis induction by all azoles tested depended on singlet oxygen action, as it was blocked by histidine. This indicates that catalase has to be inactivated by singlet oxygen before intercellular ROS signaling can induce apoptosis. If the catalase is directly inhibited by 3-AT, singlet oxygen is not required and does not contribute to apoptosis induction. Further analysis (data not shown) revealed that the action of singlet oxygen is necessary during the first hours of the experiments, whereas ROS signaling is necessary throughout the experiment.

Figure 6:
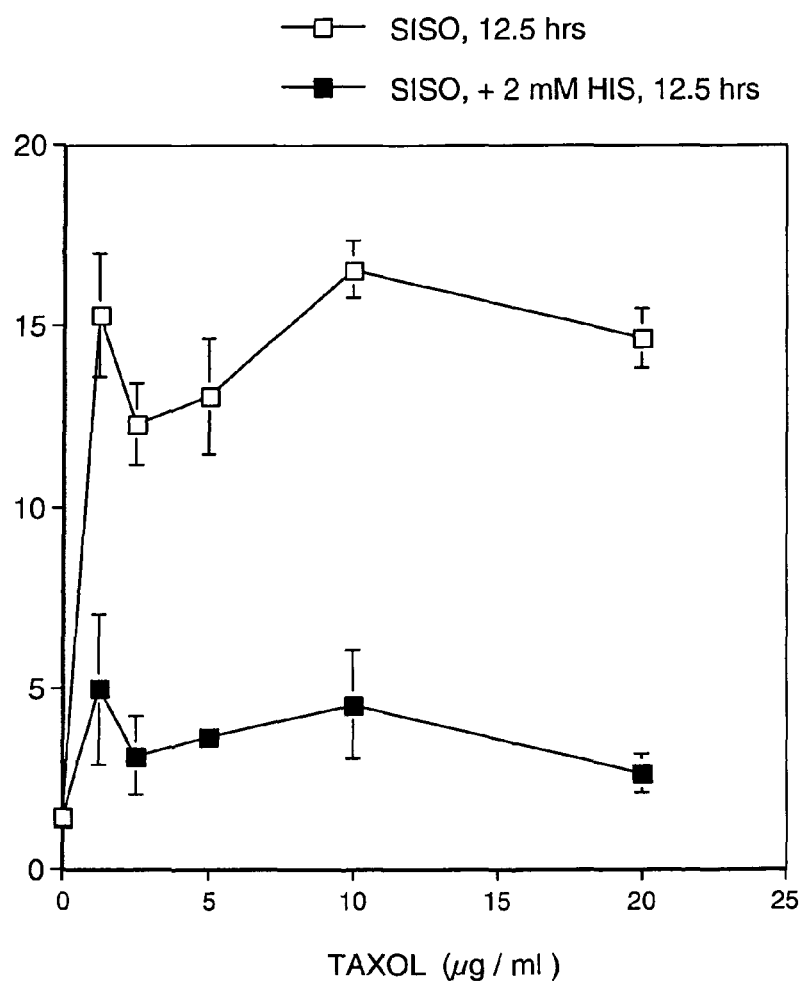

FIG. 6 discloses experimental data obtained with 25000 SISO cells (human cervix carcinoma) cultured in 48 well tissue culture clusters in the presence of the indicated concentrations of the established chemotherapeutic compound taxol. The assays contained 2 mM Histidine or not. The experiment demonstrates the unexpected finding that the apoptosis inducing effect of taxol depends on the action of singlet oxygen, as it is inhibited by the specific singlet oxygen scavenger histidine.

Figure 7:
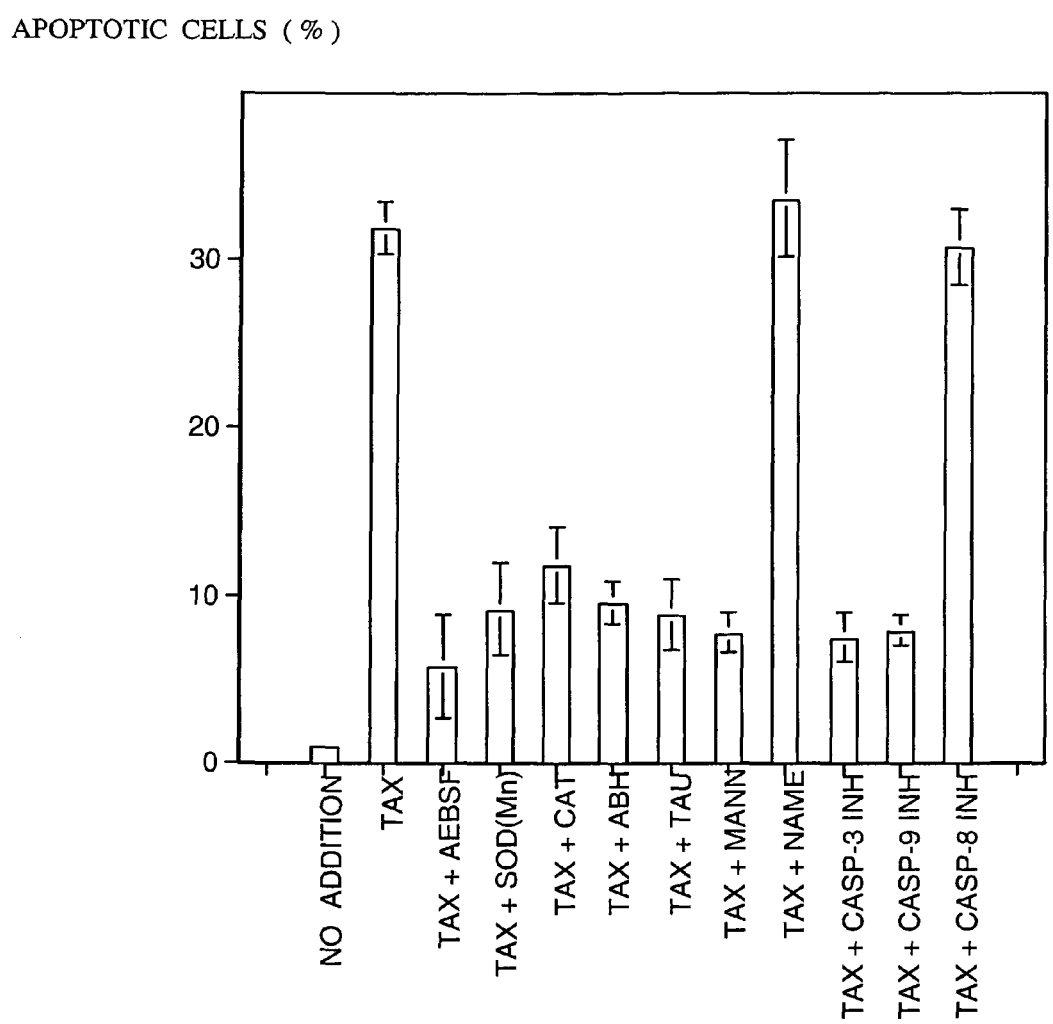

FIG. 7 discloses experimental data obtained with 25000 SISO cells (human cervix carcinoma) cultured in 48 well tissue culture clusters either in the absence of any inducer ("no addition") or in the presence of 10 µg/ml taxol ("TAX") without further additions or with the addition of 100 µM of the NADPH oxidase inhibitor AEBSF, 100 U/ml of the superoxide anion scavenger SOD (Manganese-containing SOD from E. coli), 100 U/ml catalase, 150 µM of the peroxidase inhibitor ABH (aminobenzoylhydrazide), 50 mM of the HOCl scavenger taurine, 1 mM of the hydroxyl radical scavenger mannitol, 2.4 mM of the NO synthase inhibitor L-NAME, and 25 µM of the inhibitors for caspase 3, –9 and 8. The experiment demonstrates that apoptosis induction by 10 µg/ml taxol depends on intercellular ROS signaling (HOCl pathway), as removal or inhibition of either superoxides, hydrogen peroxide, peroxidase, HOCl, hydroxyl radicals blocks apoptosis induction. The NO pathway plays no role under these conditions. Apoptosis induction is mediated by caspases 9 and 3 (mitochondrial pathway) and is independent of the death receptor specific caspase 8. The signaling chemistry during taxol-mediated apoptosis induction in human SISO cells depends on the concentration of taxol. When 2 µg/ml of taxol are used instead of 10 µg/ml, intercellular signaling is only marginally dependent on the HOCl pathway, but the NO signaling pathway is dominant.

Figure 8:
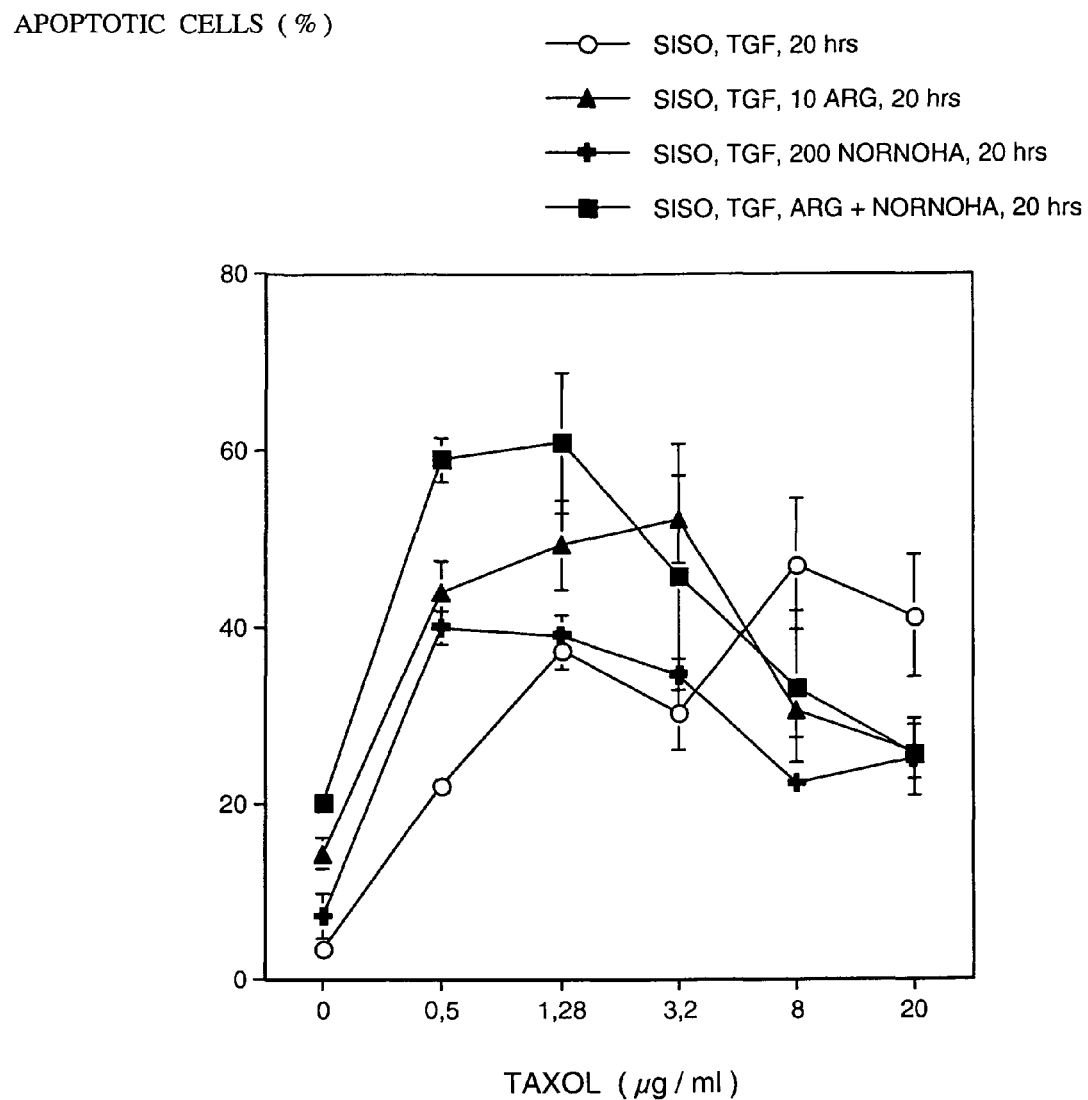

FIG. 8 discloses experimental data obtained with 25 000 SISO cells in 48 well tissue culture clusters in the presence of 20 ng/ml TGF and the indicated concentrations of taxol. Where indicated, taxol containing assays received 10 mM arginine (10 ARG), 200 µM Nor-NOHA or a combination of both. The experiment demonstrates the synergistic effect between arginine and Nor-NOHA with taxol.

Figure 9:
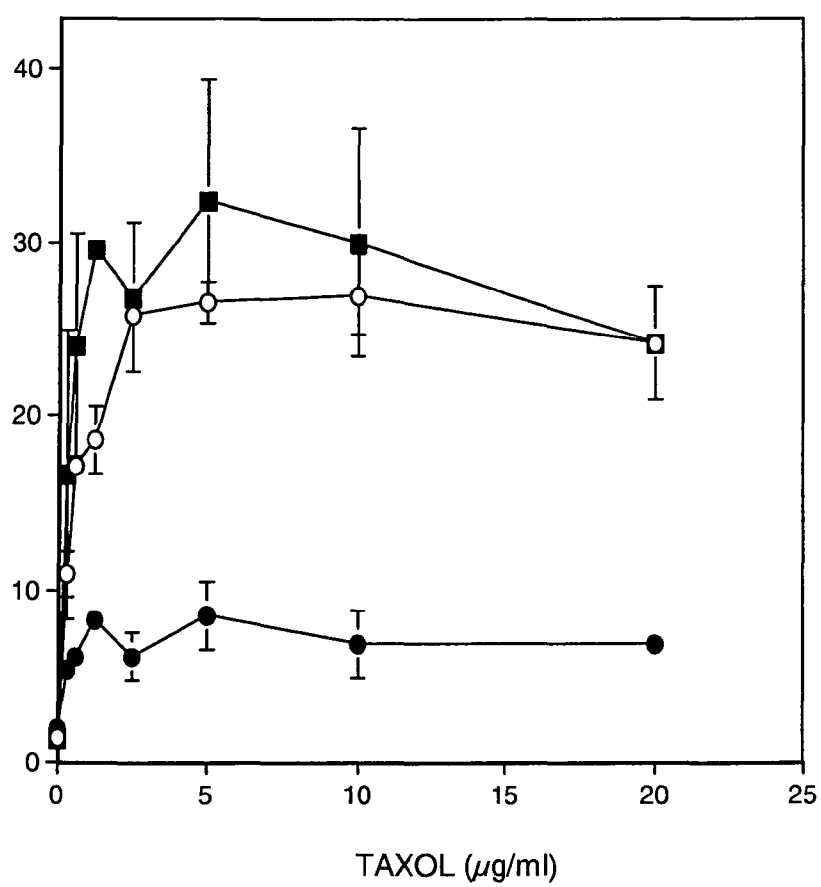

FIG. 9 discloses experimental data obtained with 12500 SISO cells in 96 well tissue culture clusters in the presence of 20 ng/ml TGF and the indicated concentrations of taxol. Furthermore, histidine was added at different time points in the experiment. The experiment demonstrates that the addition of histidine at the beginning of the experiment inhibits the destruction of the catalase, whereas an addition of histidine 5 hours after beginning of the experiment leads to a high cell apoptosis.

Figure 10:
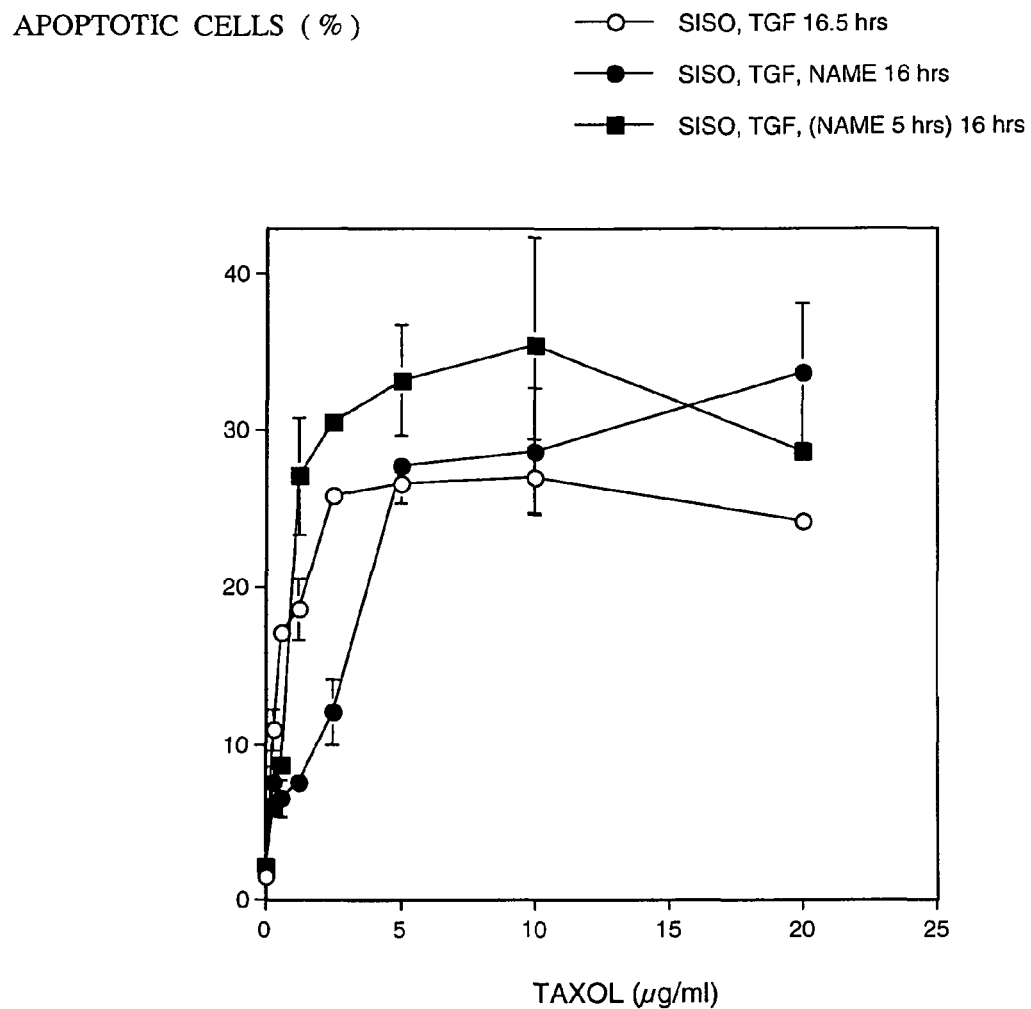

FIG. 10 refers to an experiment which was similar to the one described with respect to FIG. 9, whereas histidine was substituted by L-NAME (2.4 mM, NO-synthase inhibitor). The experimental data show that the early addition of L-NAME inhibits tumor apoptosis induced by taxol in the concentration range from zero to 5 µg/ml, whereas the late addition of L-NAME (5 hours after beginning of the experiment) only inhibits tumor apoptosis at taxol concentrations lower than 1.25 µg/ml. (The lack of inhibition of apoptosis induced by taxol at concentrations of 5 µg/ml and higher is due to exhaustion of the inhibitory system at these concentrations of taxol).

Figure 11:
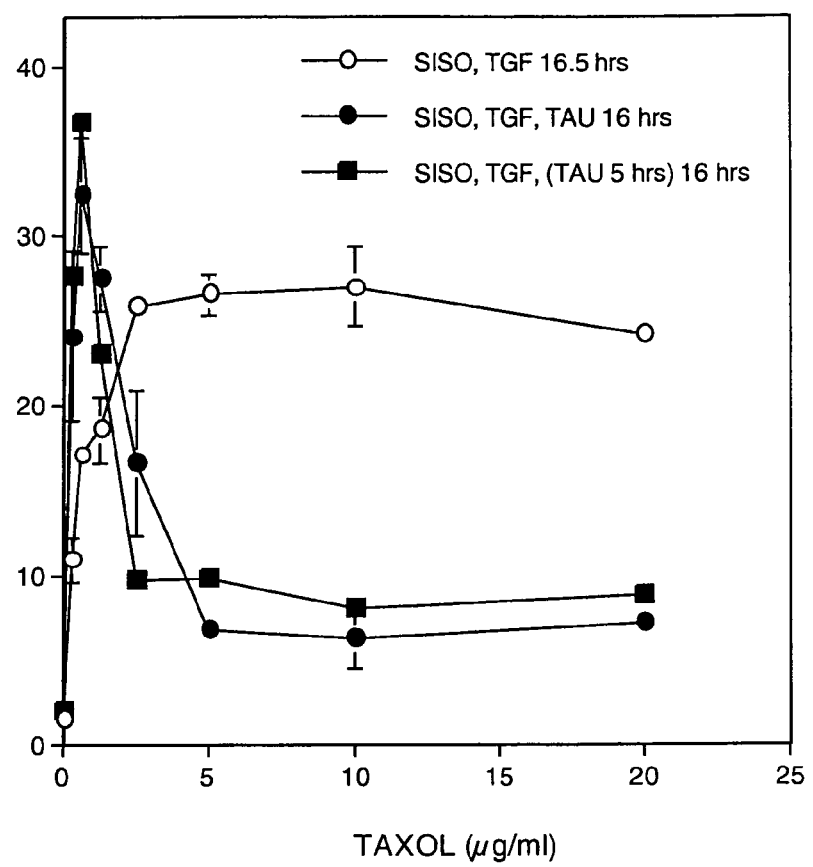

FIG. 11 refers to a similar experiment as described with respect to FIG. 8 or 9, whereas histidine/L-NAME was substituted by taurine (50 mM, scavenger of HOCl). The experimental data show that taurine only inhibits tumor apoptosis at high taxol concentrations, which indicates that only high concentrations of taxol induce apoptosis by the HOCl pathway. Furthermore, the tumor apoptosis does not depend on the point of time of addition of taurine because taurine does not influence the destruction of the catalase.

EXAMPLE 1

The proof of concept for the ROS signaling pathway of the tumor cell apoptosis through formation of singlet oxygen followed by signaling based on the interaction of reactive oxygen species is given in the following Experiments have been carried out using the photodynamic therapy on tumor cells in combination with compounds related to the ROS signaling (compare FIG. 2). L 929 cells (25 000 per 48 well tissue culture cluster in 200 µl medium containing 5% fetal bovine serum) obtained 10

μg/ml photofrin. The experiment was performed close to darkness. Controls (plus 20 ng/ml TGF-beta) were not illuminated and were wrapped in aluminium foil when incubated at 37° C. for 48 hours. All other assays received illumination by visible light for ten minutes. Assays received 20 ng/ml TGF and remained either without further addition ("Photo/Light") or received 2 mM of the singlet oxygen scavenger histidine, 50 μg/ml of the NADPH oxidase inhibitor apocynin, 100 U/ml of SOD, 50 mM of the HOCl scavenger taurine, 1 mM of the hydroxyl radical scavenger mannitol, 2.4 mM of the NO synthase inhibitor L-NAME or 40 μM of the peroxynitrite decomposition catalyst FeTPPS.

Figure 2:
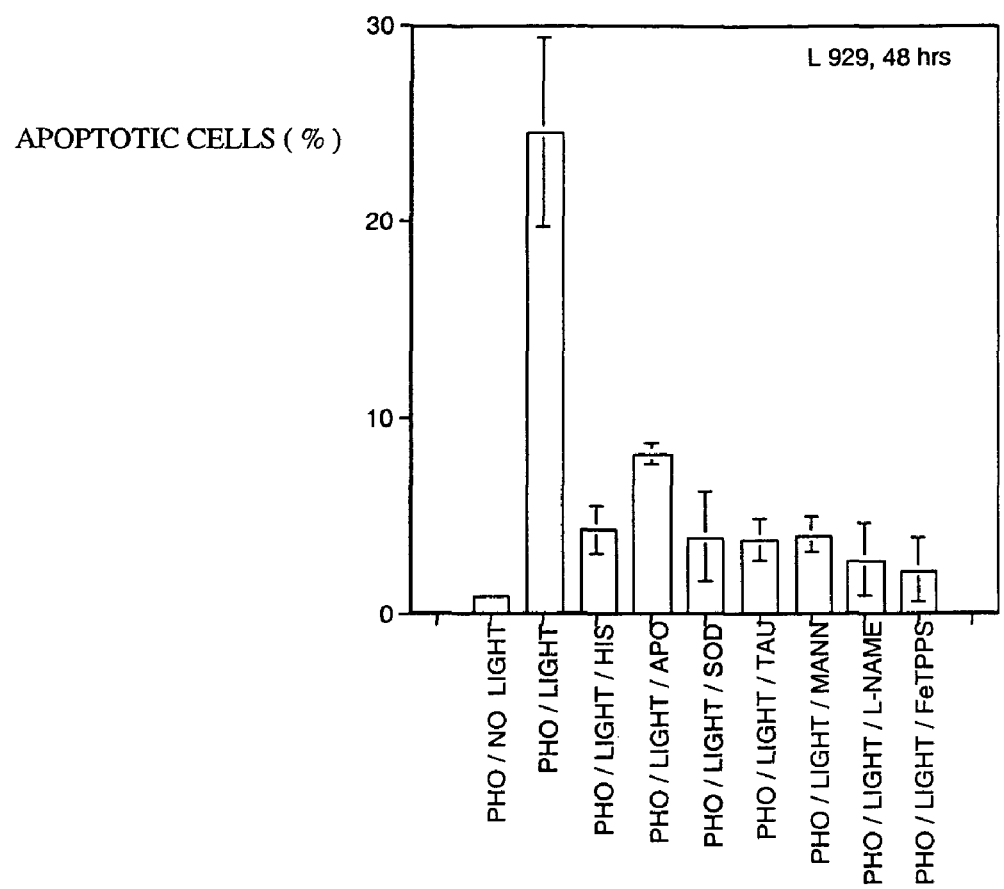
FIG. 2 discloses experimental data performed under conditions of photodynamic therapy. The figure discloses the percentage of apoptotic cells in samples comprising photofrine and compounds influencing the ROS signaling pathway, whereas the samples are optionally radiated with light. Abbreviations: PHO=photofrine; HIS=histidine; APO=Apocynin; SOD=superoxide dismutase; TAU=taurine; FeTPPS=5,10,15,20-TETRAKIS (4-sulfonatophenyl)prophyrinato iron (III), chloride.

The first experiment (starting from the left) displayed in FIG. 2 represents a control experiment and indicates a very small apoptosis in tumor cells with photofrine and no light. The second experiment shows a high apoptosis in tumor cells with photofrine and light. The third experiment comprises a combination of photofrine, light and histidine and proves that the singlet oxygen is involved in the apoptosis induction, because histidine as a singlet-oxygen inactivator reduces the apoptosis of the tumor cells. The use of photofrine, light and APO (NADPH oxidase inhibitor) SOD (superoxide dismutase, a scavenger for superoxide anions) indicates that prevention of superoxide anion synthesis or their removal from the system reduces the apoptosis by inhibiting the ROS signaling pathway. The inhibitory effect of taurine points to the role of HOCl for apoptosis induction by illuminated photofrin, whereas the inhibitory effect of the hydroxyl radical scavenger mannitol illustrates the role of hydroxyl radicals (derived from the reaction of superoxide anions with HOCl). Using L-NAME in combination with photofrine and light reduces the apoptosis in tumor cells by inhibition of the nitric oxide synthase, pointing to the role of NO. The last experiment indicates that the use FeTPPS is also able to reduce the apoptosis in tumor cells, whereas FeTPPS acts as a peroxynitrite inactivator, which proves that the apoptosis is mediated by peroxynitrite, a reaction product between NO and superoxide anions.

Taken together, the experiments prove that singlet oxygen (which is generated by illumination of photofrin) triggers apoptosis in tumor cells. In contrast to the presently accepted concept of photodynamic therapy, the role of the singlet oxygen is not to directly induce apoptosis but to destroy protective catalase of tumor cells and thus to allow the establish intercellular ROS signaling by tumor cells, leading to the apoptotic destruction of these cells. As this signaling is based on superoxide anion generation which is a specific feature of tumor cells, apoptosis induction is selectively directed against malignant cells. Whereas singlet oxygen is generated by addition of photosensitizers like photofrin during the photodynamical therapy, the present invention generates the reactive oxygen species by increasing the nitric oxide level, subsequently the nitric oxide reacts with nitrogen peroxide which reacts with hydrogen peroxide to form singlet oxygen. The following chain of reactions is then similar to those defined in FIG. 2.

EXAMPLE 2

Figure 3:
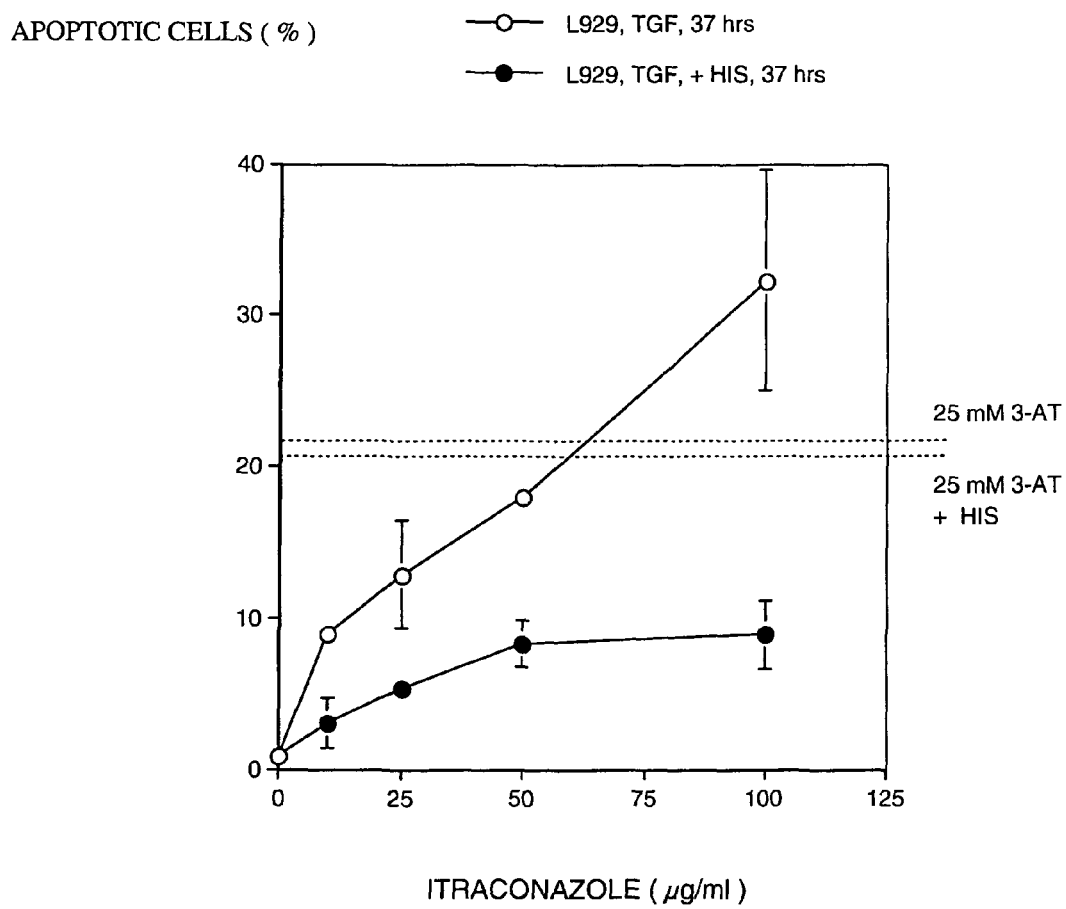
FIG. 3 discloses experimental data obtained with 25000 L929 cells in 48 well tissue culture clusters in the presence of 20 ng/ml TGF-beta. Itraconazole was added at the indicated concentrations, in the presence or absence of 2 mM histidine (singlet oxygen scavenger). The percentage of apoptotic cells was determined after 37 hrs. Please note that apoptosis is induced by itraconazole in a concentration dependent manner. Itraconazole-mediated apoptosis is significantly inhibited by the singlet oxygen scavenger histidine.

FIGS. 3-5 demonstrate that the interaction of azoles with tumor cells causes ROS-driven apoptosis, based on the initial inactivation of the protective catalase by singlet oxygen, followed by the establishment of intercellular ROS-mediated signaling. FIG. 3 demonstrates the concentration-dependent potential of itraconazole to induce apoptosis in the tumor cell L929. As apoptosis induction is blocked by the singlet oxygen scavenger histidine, singlet oxygen plays a central role for the observed effect. If catalase is blocked directly by inhibitors like 3-AT, singlet oxygen does not seem to play any role, as there is no inhibition by histidine in this case.

A modification of this experiment (data not shown) in which histidine was added at different time points allowed the conclusion that the action of singlet oxygen takes place during the first hours after contact between the cells and itraconazole and is then followed by ROS-mediated signaling in which singlet oxygen plays no further role. Singlet oxygen generation by itraconazole is well explained by the inhibitory effect of this compound on nitric oxide dioxygenase. Inhibition of this NO consuming enzyme causes a rapid increase of the NO level, followed by peroxynitrate formation when NO interacts with superoxide anions. The interaction of peroxynitrite with hydrogen peroxide then causes the generation of singlet oxygen which has the potential to inactivate protective catalase of tumor cells.

FIG. 4 demonstrates that different azoles show the potential for apoptosis induction in tumor cells. In the concentration range used in these experiments, the azoles have no effect on nontransformed cells (data not shown). FIGS. 5A-G demonstrate that various azoles induce apoptosis in the human neuroblastoma cell line SKNMC. Again, singlet oxygen is of central importance, as the reaction is blocked by histidine. According to our experiments, neuroblastoma cells have been shown to establish mainly the NO/peroxynitrite signaling pathway and not the HOCl pathway, when their catalase is inhibited or inactivated. This preference is explained by the much lower release of peroxidase from neuroblastoma lines compared to cell lines like L929 or SISO. In line with this finding, the action of the azoles as shown in FIGS. 5 A-G is inhibited by an inhibitor of superoxide anion generation (AEBSF) and a highly specific of the nNOS-specific inhibitor 3-Br-7-NI.

These data show the uniform reaction of various azoles: generation of singlet oxygen, catalase inhibition, establishment of tumor cell-driven intercellular ROS signaling, here based on NO and superoxide anions (leading to the generation of the ultimate apoptosis inducer peroxynitrite). FIG. 5 H demonstrates the direct inhibition of the tumor cell catalase by 3-AT leads to the same pattern of intercellular ROS signaling as seen for the action of azoles, however without an involvement of singlet oxygen. Taken together, these data confirm that singlet oxygen is not part of intercellular signaling and ultimate apoptosis induction but represents the initial trigger to inactivate tumor cell catalase.

EXAMPLE 3

FIG. 6 shows that apoptosis induction by the well-known antitumor drug taxol depends on the action of singlet oxygen, as it is blocked by histidine. It thus resembles the azoles in this respect. This finding is novel, unexpected and, for the first time, allows to understand the selectivity of taxol for tumor cells. After action of singlet oxygen (generated by taxol through the same mechanisms as outlined for the azoles in example 2), taxol-treated tumor cells die through intercellular signaling which involves superoxide anions (as the reaction is blocked by AEBSF and SOD), hydrogen peroxide (as it is blocked by catalase), peroxidase (as it is blocked by ABH), HOCl (as it is blocked by taurine), hydroxyl radicals (as it is blocked by mannitol). These components represent the central players of the HOCl signaling pathway (as outlined in FIG. 1). NO does not seem to play an important role under these conditions, as L-NAME does not block the reaction. If the concentration of taxol is lowered, the NO pathway becomes more prominent (data not shown).

Finally the use of specific caspase inhibitors demonstrates the role of mitochondrial apoptosis regulation and gives no indication for the involvement of death receptors, as the caspase-8 inhibitor has no effect.

Finally, FIG. 8 demonstrates a synergistic effect between suboptimal concentrations of taxol with arginine and the arginase inhibitor nor-NOHA.

These experiments illuminate the activity of taxol and demonstrate that it acts through the chain of events that are the center of this patent application. This may indicate that the pathways worked out in vivo may well function in vivo.

EXAMPLE 4

In the following, taxol was subjected to the test according to the present invention in order to determine its tumor inducing properties due to an inactivation of a catalase on the tumor cell surface.

Step 1

Human SISO cells are used in a 48-well plate (Costar) in 200 µl media with a cell concentration of 25,000. The media comprises 20 ng/ml TGF-beta and furthermore Taxol subjected for testing in a concentration ranging from 1.25-20 ng/ml. For comparison, control experiments are performed without Taxol which is tested for apoptosis induction. As shown in FIG. 6, taxol induced apoptosis already occurs after 12.5 hours at all concentrations, whereas the assay without addition of taxol showed background apoptosis.

Step 2

Step 2 is carried out with the same conditions as specified for step 1, whereas all cells are contacted with taxol. In addition, histidine (2 mM) is added to the cells, whereas also experiments without histidine are performed as control experiments. As shown in FIG. 6, taxol-induced apoptosis was inhibited by histidine at all concentrations of taxol applied, demonstrating that taxol-mediated apoptosis induction requires the action of singlet oxygen.

Additional step 3

The experimental conditions are the same as for step 1, whereas the cells used for step 3 are normal diploid fibroblasts. Control experiments are carried out without the test compound, and the cells are incubated for two days. Taxol did not induce significant apoptosis in the diploid fibroblasts, indicating that it does not show unspecific toxic effects under these conditions (data not shown). Likewise, the use of SISO cells with inhibited superoxide anion generation through siRNA-based genetic knockdown did not lead to taxol-mediated apoptosis induction, indicating that taxol-mediated apoptosis does depend on superoxide anion synthesis, which is a hallmark of the transformed state.

In a further experiment using the conditions of step 1, human tumor cells (SISO) are contacted with taxol (10 µg/ml) and 100 µM of the NADPH oxidase inhibitor AEBSF, 100 U/ml of the superoxide anion scavenger SOD (Manganese-containing SOD from $E.\ coli$), 100 U/ml catalase, 150 µM of the peroxidase inhibitor ABH (aminobenzoylhydrazide), 50 mM of the HOCl scavenger taurine, 1 mM of the hydroxyl radical scavenger mannitol or 2.4 mM of the NO synthase inhibitor L-NAME. Taxol-mediated apoptosis was inhibited by the inhibitors of superoxide anion generation (AEBSF, SOD) and the inhibitors of the HOCl pathway (catalase, ABH, taurine, mannitol), but not by the inhibitor of the NO pathway (L-NAME) (FIG. 7).

When 2 µg/ml of taxol were applied instead, the NO pathway became more prominent, whereas the HOCl pathway was less effective, based on the inhibitor data (data not shown). At all concentrations of taxol, superoxide anions and one of the two pathways were effective.

EXAMPLE 5a-c

The effect of a singlet oxygen scavenger, a NO synthase inhibitor and a HOCl scavenger on either the destruction of the catalase or the HOCl pathway was determined by the following experiment. 12500 SISO cells in 100 µl media in 96 tissue wells were treated with taxol (20 µg/ml) in the presence of TGF-β (20 ng/ml). In addition, the singlet oxygen scavenger, the NO synthase inhibitor or the HOCl scavenger was added at different points of time in the experiments.

In experiment 5a, histidine (singlet oxygen scavenger) was added at the beginning of the experiment or after 5 hours. A control experiment was performed, wherein no histidine was added. FIG. 9 shows that the addition of histidine at the beginning of the experiment inhibits the tumor apoptosis to a great extend. However, the late addition (5 hours after beginning of the experiment) only shows a small effect of apoptosis inhibition. This can be explained by the properties of histidine to inhibit the destruction of the catalase. The early addition of histidine inhibits the catalase destruction, whereas a late addition of histidine (the catalase was already destroyed to a significant extend) is not able to inhibit apoptosis anymore.

Example 5b was carried out like experiment 5a, whereas L-NAME was used instead of histidine (2.4 mM, NO synthase inhibitor). FIG. 10 shows that the early addition of L-NAME inhibits tumor apoptosis, whereas the late addition of L-NAME only shows some inhibition at low taxol concentrations. The experiment demonstrates that the inhibition of the NO production inhibits the formation of reactive oxygen species and therefore inhibits the destruction of the catalase, when taxol was applied at concentrations lower than 5 µg/ml. When taxol was applied at a concentration of 5 µg/ml or higher, the inhibitory system was exhausted and the analysis of the role of NO was not possible in this concentration range.

Experiment 5c was carried out like experiments 5a and 5b, whereas taurine was used instead of histidine or L-NAME. Taurine (50 mM, HOCl scavenger) was added at the beginning of the experiment and after 5 hours in a second experiment. A control experiment was performed, wherein no taurine was added. The experimental results (see FIG. 11) demonstrate that the tumor apoptosis is independent from the time point of the addition of taurine. This can be explained, as taurine is a HOCl scavenger that does not influence the destruction of the catalase but the HOCl pathway. Experiment 5c further shows that only high concentrations of taxol induce the HOCl pathway, which is inhibited by taurine.

EXAMPLE 6

Further experiments have been carried out using different types of cells and different apoptosis inhibitors. The results of these experiments are shown in table 1 below. The experimental setup was analogue to the examples 5a-5c and the late addition of the inhibitor (histidine, L-NAME, 3-Br-7-Nitroindazole or taurine) was performed 1 hour after beginning of the experiment. The concentrations of taxol, histidine, L-NAME and taurine were the same as in the experiments 5a-5c. 3-Br-7-Nitroindazole was added at a concentration of 10 µm. The apoptosis inducing compounds were added at increasing concentrations (0-5 mM arginine, 0-20 µg/ml taxol, 0-20 µg/ml artemisine, 0-20 µg/ml xanthohumol, 0-20 µg/ml itraconazole, 0-10 µg/ml miconazole, 0-20 µg/ml antibody against Apo/FAS receptor). In each of the experiments, the effect of the inhibitors on the singlet oxygen mediated catalase destruction and/or the subsequent ROS signaling could be observed. The cell apoptosis inhibitory effect of the compounds is indicated by "+" in table 1. Addition of histidine at the beginning of the experiment caused inhibition in all experiments and for all cell lines shown. Addition of histidine one hour after the addition of the indicated inducers did not cause inhibition of apoptosis, as catalase destruction by singlet oxygen had already occurred at this time point (please see FIG. 9). The experiments using neuroblastoma cells only display apoptosis mediated by the NO pathway as these cells only release small amounts of peroxidase. Therefore, addition of the nNOS-specific inhibitor 3-Br-7NI caused inhibition of apoptosis, irrespective of the time of addition. The other cell lines displayed NO-signaling pathway mediated apoptosis at lower concentrations of the apoptosis inducing compound and HOCl mediated apoptosis at higher concentrations. Therefore, addition of L-NAME at the beginning of the experiment inhibited apoptosis at all concentrations of inducers (reflecting the role of singlet oxygen generation from NO-derived peroxynitrite), whereas addition of L-Name at one hour after addition of the inducer only inhibited apoptosis induced by lower concentrations of inducers, indicating that under those conditions the NO signaling pathway prevailed, as soon as catalase was destroyed. Addition of taurine in the presence of higher concentrations of inducers inhibited apoptosis irrespective of the time of addition (zero versus one hour), as HOCl is only involved in intercellular signaling, but not in catalase destruction.

TABLE 1

| | | Inhibitors | | | |
|---|---|---|---|---|---|
| Cell line | Inductor | Histidine | L-NAME | 3-Br-7-NI | Taurine |
| SISO | Taxol | + | + | | + |
| SHEP | Taxol | + | | + | |
| SKNMC | Arginine | + | | + | |
| MKN-45 | Fas antibody | + | + | | + |
| MKN-45 | Artemisinine | + | + | | + |
| Gumbus | Taxol | + | + | | + |
| Gumbus | Arginine | + | + | | + |
| Gumbus | Itraconazole | + | + | | + |
| Gumbus | Miconazole | + | + | | + |
| Gumbus | Xanthohumol | + | + | | + |

The invention claimed is:

1. A method for identifying compounds that induce tumor apoptosis by inactivating a catalase on a tumor cell surface, said method comprising the following steps:
   (1) contacting test compounds with tumor cells or transformed cells and selecting those test compounds that induce apoptosis in said tumor or transformed cells;
   (2) determining whether the apoptosis observed in step (1) arises from the inactivation of tumor cell catalase by: (a) contacting the tumor apoptosis-inducing test compounds identified in the step (1) with tumor cells in a medium comprising histidine and (b) selecting those test compounds that that reduce or inhibit apoptosis-induction in said tumor cells under this condition as compared to the apoptosis-induction observed in step (1); and
   (3) identifying the test compounds selected in part (b) of step (2) as compounds that induce tumor apoptosis by inactivating tumor cell catalase.

2. The method according to claim 1, wherein the first step comprises supplying TGF-β to the cells.

3. The method according to claim 1, wherein the method is performed in the absence of non-tumor cells or non-transformed cells.

4. The method according to claim 1, further comprising the step of determining whether the compounds are toxic to non-tumor cells.

5. The method according to claim 1, further comprising the step of determining whether the inhibition of tumor apoptosis by histidine is based on ROS (reactive oxygen species) signaling.

6. The method according to claim 5, wherein the step of analyzing the effect on ROS signaling is performed by contacting the test compounds with tumor cells and supplying a first compound, said first compound characterized in that it is able to lower the level of a second compound selected from the group consisting of: superoxide anions, hydrogen peroxide, peroxidase, HOCl, hydroxyl radical, nitric oxide, hydroxyl radical, peroxynitrite, further wherein lowering the level of this second compound reduces the effect of tumor apoptosis induced by the test compound.

* * * * *

UNITED STATES PATENT AND TRADEMARK OFFICE
CERTIFICATE OF CORRECTION

| | | |
|---|---|---|
| PATENT NO. | : 8,288,088 B2 | Page 1 of 1 |
| APPLICATION NO. | : 12/438791 | |
| DATED | : October 16, 2012 | |
| INVENTOR(S) | : Georg Bauer | |

Figure 1:
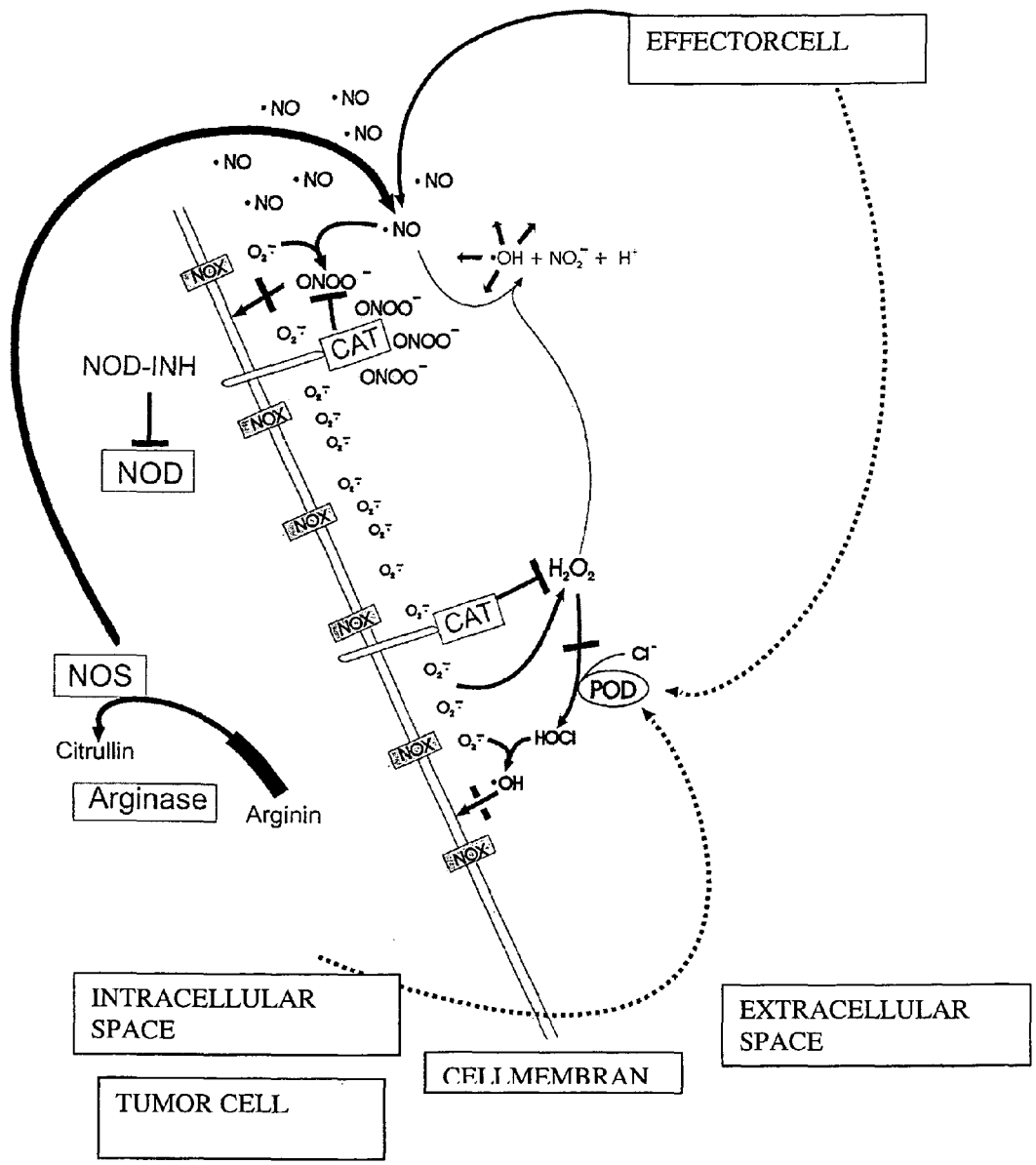
FIG. 1 discloses the mechanisms of apoptosis in tumor cells. Abbreviations: NOS=nitric oxide synthase; NOD=nitric oxide dioxygenase; NOD—INH=nitric oxide dioxygenase inhibitor; CAT=catalase; POD=peroxidase; NOX=NADPH oxidase.

It is certified that error appears in the above-identified patent and that said Letters Patent is hereby corrected as shown below:

In drawing sheet 1, in the caption at the bottom of Figure 1, replace the term "CELL MEMBRAN" with the corrected spelling --CELL MEMBRANE--.

In column 1, line 6, replace the term "PCT/E07/006964" with the correct application number --PCT/EP07/006964--.

In column 18, line 11 (claim 1), delete the word "the" between --in-- and --step (1)--.

In column 18, line 13 (claim 1), delete the second iteration of the word "that".

Signed and Sealed this
Twenty-ninth Day of January, 2013

David J. Kappos
*Director of the United States Patent and Trademark Office*